United States Patent
Aristovich et al.

(10) Patent No.: US 6,340,777 B1
(45) Date of Patent: Jan. 22, 2002

(54) METHOD FOR PURIFYING ACETONE

(75) Inventors: Valery Jurievich Aristovich; Yury Valerievich Aristovich, both of Sankt-Petersburg (RU); John William Fulmer, Mt. Vernon, IN (US); Andrey Jurievich Sokolov, Sankt-Petersburg (RU)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/668,996

(22) Filed: Sep. 25, 2000

(30) Foreign Application Priority Data

Oct. 22, 1999 (RU) .......................................... 99121965

(51) Int. Cl.$^7$ .............................................. C07C 45/78
(52) U.S. Cl. ........................................................ 568/411
(58) Field of Search ......................................... 568/411

(56) References Cited

U.S. PATENT DOCUMENTS

| | | |
|---|---|---|
| 1,542,538 A | 6/1925 | Willkie |
| 2,906,676 A | 9/1959 | Bewley et al. |
| 2,971,893 A | 2/1961 | Hood |
| 3,129,147 A | 4/1964 | Codignola |
| 3,668,256 A | 6/1972 | Brundege |
| 4,113,780 A | 9/1978 | Strehlke et al. |
| 4,329,510 A | 5/1982 | Uno et al. |
| 4,336,109 A | 6/1982 | Hosaka et al. |
| 4,340,447 A | 7/1982 | Laverick et al. |
| 4,501,645 A | 2/1985 | Berg et al. |
| 4,584,063 A | 4/1986 | Berg et al. |
| 4,620,901 A | 11/1986 | Berg et al. |
| 4,626,600 A | 12/1986 | Fulmer et al. |
| 4,722,769 A | 2/1988 | Chan et al. |
| 4,931,145 A | 6/1990 | Berg |
| 5,399,776 A | 3/1995 | Fraini et al. |
| 5,567,853 A | 10/1996 | Gupta |
| 5,762,764 A | 6/1998 | Chang et al. |
| 5,788,818 A | 8/1998 | Lorenzoni et al. |

FOREIGN PATENT DOCUMENTS

| | | |
|---|---|---|
| BG | 60818 B1 | 4/1991 |
| CS | 229 772 B | 6/1984 |
| EA | 000053 B1 | 4/1998 |
| EP | 0085289 | 8/1983 |
| GB | 2116177 | 9/1983 |
| SU | 288745 A | 4/1973 |
| SU | 1232 665 | 5/1986 |

OTHER PUBLICATIONS

Foriegn Search Report for Russian Patent Application No. 99121965, filed Oct. 22, 1999.

PCT International Search Report for International Application No. PCT/US 00/27095, International Filing Date Oct. 10, 2000.

*Primary Examiner*—Sreeni Padmanabhan
*Assistant Examiner*—Sikarl A. Witherspoon

(57) ABSTRACT

A process is described for purifying acetone from a crude acetone-phenol mixture produced upon oxidizing cumene. In the process, an alkaline agent and an oxidizing agent are both added to the mixture to help remove aldehyde contaminants upon purification.

10 Claims, No Drawings

METHOD FOR PURIFYING ACETONE

The present application is a U.S. non-provisional application based upon and claiming priority from Russian Patent Application No. 99121965, which is hereby incorporated by reference.

BACKGROUND OF THE INVENTION

The invention concerns a method for purifying acetone obtained from cumene by a combination of rectification and chemical processing to remove aldehyde impurities in order to produce high-quality commercial-grade acetone.

In a known method (U.S. Pat. No. 4,626,600) for obtaining acetone from cumene, cumene is oxidized with air to produce an intermediate cumene hydroperoxide, which is then decomposed with sulfuric acid to give a crude acetone-phenol mixture containing a number of impurities. This method is described, for example, in U.S. Pat. No. 4,626,600. The crude acetone-phenol mixture then undergoes rectification to separate a low-boiling "crude acetone fraction" containing acetone, water, cumene, aldehydes and alpha-methylstyrene, and a "crude phenol fraction" containing phenol and high-boiling compounds such as acetophenone and resins. The crude acetone fraction is further purified by rectification and/or chemical processing to produce commercial-grade acetone.

It is known that the "crude acetone fraction" referred to above contains small amounts of aliphatic aldehydes, olefin and carbonyl impurities, specifically acetaldehyde, propionaldehyde, isobutylaldehyde, mesityl oxide, diacetone alcohol and hydroxyacetone, which are formed as by-products in the cumene hydroperoxide decomposition stage described above. Using only ordinary distillation technology to purify this fraction of the crude acetone is inefficient, since these aldehydes and the olefin impurities remain in the purified product, lowering its purity and quality. Therefore, to obtain a high-purity product not containing acetone aldehydes the purification methods must be improved by the following methods.

U.S. Pat. No. 4,620,901 describes a special technology for an extractive distillation, using dimethylformamide as a selective solvent to remove the aldehydes to a low level. But this method is made complicated by the fact that it requires expensive distillation equipment and produces acetone of unsatisfactory quality containing traces of solvent as an impurity that make the acetone unusable by most final end users.

U.S. Pat. No. 5,567,853 likewise describes a method which requires complex technology for extractive distillation by reacting the acetone fraction with a glycol solution containing compounds of alkali metals. But this method uses expensive solvents that can be regenerated only by using an additional distillation column, and the method produces a commercial acetone having a purity of only 98.3% w/w, which is not suitable for users of high-purity acetone, for example in the production of polycarbonate plastic.

A number of methods are known for chemical treatments involving alkali metal hydroxides (See, e.g., U.S. Pat. No. 4,722,769 and U.S. Pat. No. 4,340,447) to carry out the aldol condensation of low-boiling aldehydes that result in their converting to high-boiling aldol derivatives that are later removed from the acetone by ordinary distillation. The problem with this technology is that the aldol derivatives formed are thermally unstable and decompose in the boiler of the distillation column, liberating low-boiling aldehydes that penetrate to the top of the column and contaminate the acetone. In the method described in U.S. Pat. No. 4,340,447, a special distillation procedure with sidebar distillation is used to avoid this problem. This procedure complicates and interferes with control of the process, and in certain cases the acetone produced is not aldehyde-free, and therefore not suitable for an end use in polycarbonates.

One goal of the invention was to design a method for purifying acetone that would produce a higher quality product.

This invention represents a reliable, simple and economical process for removing aldehydes and olefin impurities from acetone by oxidizing the impurities present in the crude acetone fraction using an oxidizing agent added in an amount such that the acetone itself is not adversely affected in the production of high-quality aldehyde-free commercial-grade acetone.

BRIEF SUMMARY OF THE INVENTION

In the method of the invention, the crude acetone obtained from the process for manufacturing Cumene-Phenol, which contains acetone, water, aldehydes, cumene and alpha-methylstyrene, is fed to a set-up for purifying acetone consisting of two rectifying columns. In the first rectifying column, most of the low-boiling impurities of the acetone, including various aldehyde contaminants, are evaporated and removed as overhead product. All the remaining constituents, including the acetone, are removed from the column bottom and are fed to the second rectifying column. In the second rectifying column the acetone is purified of water and other high-boiling impurities and is removed in the form of distillate, while the water, cumene, alpha-methylstyrene and other high-boiling constituents are removed from the column's distilling flask. In the method of the invention, an alkaline agent and an oxidizing agent are added separately or together to the feed of one or both of the rectifying columns. The alkaline agent and oxidizing agent can be added virtually anywhere in the process in the second column or upstream, but it is more efficient to add both agents somewhere before the second rectification column.

The acetone purification process is preferably accomplished at an alkaline to oxidizing agent ratio of 1:0.01–1:100 in the first column feed, with the oxidizing agent being supplied at a rate of 0.05–50 g per 1000 ml of the first column feed. The oxidizing reagent is preferably fed in the form of a 0.1–20% aqueous solution.

DETAILED DESCRIPTION OF THE INVENTION

The oxidizing agent used may be hydrogen peroxide or another inorganic oxidizing agent, including such inorganic peroxide compounds as $KMnO_4$, etc.

In a number of cases the base and the oxidizing agent are mixed prior to distillation.

A distinguishing feature of this invention is the special chemical treatment during the distillation of the crude acetone fraction with a two-component mixture consisting of an oxidizing and an alkaline agent. The two reagents used in the chemical treatment may be added separately or mixed, either to one of the rectifying columns or to both rectifying columns, using different places for feeding them, to optimize the oxidizing reactions and to remove the aldehyde impurities in the production of high-quality commercial-grade acetone, without negatively affecting the quality of the acetone by peroxidation. In a most preferred embodiment, both the oxidizing and alkaline agent are added to both rectifying columns. The alkaline agent and the oxidizing agent may be added either to the feed stream before it enters the columns or to the liquid in the sumps of the columns. The oxidizing agents used are hydrogen peroxide, sodium peroxide, potassium permanganate and sodium permanganate. The alkaline reagents used are alkaline metal hydroxides and carbonates. These reagents can be mixed together in advance or they can be mixed inside the distillation column.

The essence of the method, as compared to known methods, consists in that, when the combined feed of the oxidizing and the alkaline reagents are present in the selected ratio, the optimal removal of aldehydes and unsaturated impurities is achieved with no harmful side-reactions for the acetone. In the present invention the ratio of the alkaline reagent to the oxidizing reagent achieved in the rectifying column should be held within a weight ratio range of alkali:oxidant from 1:0.1 to 1:100. The oxidizing agent is preferably fed at a rate of 0.05–50 gram per 1000 ml of crude acetone fraction feed in the form of a 0.1–20% w/w aqueous solution. The oxidizing agent can be added to the feed into one and/or both columns, and also to the top and/or bottom part of at least one of the rectifying columns. This chemical oxidation treatment theoretically converts the low-boiling compounds and unsaturated and carbonyl-type impurities into their high-boiling derivatives, which are water-soluble and stable to thermal decomposition. These high-boiling derivatives go into the flask of the second rectifying column and can be easily removed from the acetone with the bottom product without being converted back into aldehydes during the distillation process.

The "permanganate test" (permanganate time test, an oxidation test using a solution of potassium permanganate) is widely used as an analytical test for determining the total aldehydes and other reducing impurities present in commercial-grade aldehyde. The method calls for adding a small quantity of potassium permanganate to a sample of acetone and measuring the time required for the color to dissipate. A longer color dissipation time (the permanganate time) indicates a lower content of reducing substances in the sample and a higher quality of the acetone. Most of the acetone sold on the market must have a minimum permanganate time of 2 hours, but this may be difficult to achieve if the manufacturing plant is overloaded and is operating at above design capacity. As a result, typical permanganate times range from 0.5 hour to 3 hours for aldehyde contents of more than 50 ppm in the commercial-grade acetone. If the time is longer than 5 hours, the aldehyde content is below 10 ppm and the quality of the acetone is considered to be excellent.

In addition to permanganate time, there are other important indicators of the quality of commercial-grade acetone, including water content and content of diacetone alcohol, which must be held at <0.3% w/w and <30 ppm, respectively. It is important to note that these quality indicators are not violated when the proposed technology of the present invention is used to remove aldehydes.

The examples and tables below are for the purpose of illustrating the invention and do not restrict it. All U.S. Patents referenced in this document are incorporated by reference herein.

EXAMPLE 1
(Example for comparison)

A stream of crude acetone fraction obtained from the standard Cumene-Phenol process, containing up to 65% acetone and corresponding amounts of water, cumene and alpha-methylstyrene is fed to a two-column rectifying set-up to be purified. This fraction also contains minor amounts, on the ppm level, of components such as acetaldehyde, propionaldehyde, methanol, mesityl oxide, diacetone alcohol, and phenol.

The crude acetone fraction having the composition indicated above is supplied at a temperature of 49–50° C. to the first rectifying column, which has an efficiency of 20–30 theoretical plates. A 20% aqueous solution of NaOH is supplied to the distilling flask of this same column at a rate of 3.3 g per 1000 ml of crude acetone feed. The temperature at the top of the first column is held at 55–56° C. by using a high reflux ratio, with the small overhead fraction being withdrawn in the form of vapor at a rate of 1–2% of the weight of the feed stream, the vapor containing the greater part of the low-boiling impurities, including acetaldehyde, which condenses and is withdrawn as a by-product. The temperature of the flask is held at 75–80° C., and the bottom fraction, accounting for 98–99% of the weight of the feed stream, containing acetone, cumene, alpha-methylstyrene, water and various impurities, is sent on to the second rectifying column for further treatment. The second column had an efficiency of 45–55 theoretical plates and operated at a pressure at the top of the column of 500 mm Hg and a vapor temperature of 44–45° C. The acetone is withdrawn from the top of the column in the form of vapor, completely condensed and a portion of the liquid is drawn off in the form of the end product, and another portion is returned to the top of the column in the form of reflux in a ratio of 1:2.0–2.5. The quality of the commercial-grade acetone obtained was verified by the permanganate time test and a value of 2.5 hours was obtained. The two-phase bottom product from the second distillation column contains the aqueous, cumene, and alpha-methylstyrene components of the feed stream with traces of carbonyls, aldol condensation products, phenol, and NaOH residues.

EXAMPLES 2–11

A series of experiments was undertaken using the crude acetone fraction similar in composition to that used in Example 1. The temperature, pressure and reflux ratio values for the two rectifying columns were likewise analogous to those used in Example 1. In examples 2–10, the aqueous solution of oxidizing agent $H_2O_2$ was added to the rectifying column at different input places in the amounts indicated in Table 1. In Examples 1–3, 5, and 7–11 the oxidizing agent was added in the form of a 5% aqueous solution of $H_2O_2$, in Example 4 it was added in the form of a 3% aqueous solution, in Example 6 it was added in the form of a 10% aqueous solution. The amounts of NaOH alkaline reagent added in Examples 2–10 are as shown in Table 1. The results of the experiments in Table 1 and Table 2 show that the quality of the acetone improved significantly: the permanganate times, in all instances except Example 2, were longer than 5 hours. Table 2 likewise shows that the remaining critical quality indicators for acetone, namely the contents of water of diacetone alcohol, remained within the limits of the standard in all

EXAMPLE 12

In Example 12, a 2.5% aqueous solution of $KMnO_4$ was added as the oxidizing agent. All of the other conditions remained as in Example 1. As shown in Table 2, the permanganate time obtained for the acetone was >5 hours.

TABLE 1

| No. | Supply of solution of oxidizing agent | | Supply of NaOH solution |
|---|---|---|---|
| | Solution Grams of oxidizing agent/1000 ml of feed | H₂O₂ Place supplied | Amount (g) of NaOH/ 1000 ml of feed |
| 1 | — | — | 3.3 |
| 2 | 0.37 | Into feed of column 1 | 3.3 |
| 3 | 0.74 | Into feed of column 1 | 3.3 |
| 4 | 0.89 | Into feed of column 1 | 3.3 |
| 5 | 1.48 | Into feed of column 1 | 3.3 |
| 6 | 3.00 | Into feed of column 1 | 3.3 |
| 7 | 1.48 | Into feed of column 1 | 0.5 |
| 8 | 1.48 | Into top of column 1 | 3.3 |
| 9 | 1.48 | Into flask of column 1 | 3.3 |
| 10 | 1.48 | Into feed of column 1 | 3.3 |
| 11 | 1.48 | Into feed of column 1 (mixed with NaOH immediately before being fed) | 3.3 |
| | 2.5% solution | KMnO₄ | |
| 12 | 0.74 | Into bottom of column 1 | 3.3 |

TABLE 2

Results of analysis

| No. | Permanganate time, hours | DAA, ppm | H₂O, % |
|---|---|---|---|
| 1 | 2.5 | 6 | 0.25 |
| 2 | 3.1 | 6 | 0.25 |
| 3 | 5.6 | 5 | 0.30 |
| 4 | 6.3 | 4 | 0.30 |
| 5 | 8.1 | 3 | 0.25 |
| 6 | 6.5 | 3 | 0.30 |
| 7 | 9.0 | 2 | 0.25 |
| 8 | 7.0 | 3 | 0.30 |
| 9 | 7.0 | 3 | 0.25 |
| 10 | 7.5 | 3 | 0.25 |
| 11 | 7.0 | 3 | 0.25 |
| 12 | 9.0 | 2 | 0.30 |

What is claimed is:

1. A method for purifying acetone, comprising: distilling a crude acetone-phenol mixture by feeding the mixture to a first rectification column for separating low-boiling impurities; removing remaining constituents of the mixture from the bottom of the first column; and feeding the remaining constiuents to a second rectification column for separating high-boiling impurities wherein an alkaline agent and an oxidizing agent are both added to the remaining constituents in the second column or any point upstream, and wherein a ratio of the alkaline agent to the oxidizing agent is from 1:0.1 to 1:100, and the oxidizing agent is supplied at a rate of 0.5–50 grams per liter of the remaining constituents, thereby producing a purified acetone having a permanganate time of at least five hours.

2. A method for purifying acetone according to claim 1, wherein the oxidizing agent is supplied to the feed of one or both of the rectifying columns.

3. A method for purifying acetone according to claim 1, wherein the oxidizing agent is supplied to the top and/or lower part of at least one of the columns.

4. A method for purifying acetone according to claim 1, wherein the oxidizing agent is supplied in the form of a 0.1–20% aqueous solution.

5. A method for purifying acetone according to claim 1, wherein hydrogen peroxide is used as the oxidizing agent.

6. A method for purifying acetone according to claim 1, wherein inorganic oxidants are used as the oxidizing agent.

7. A method for purifying acetone according to claim 1, wherein inorganic peroxide compounds are used as the oxidizing agent.

8. A method for purifying acetone according to claim 1, wherein the alkaline agent and the oxidizing agent are mixed prior to being added.

9. A method for purifying acetone according to claim 6, wherein the inorganic oxidant comprises potassium permanganate (KMnO₄).

10. A method for purifying acetone according to claim 7, wherein the inorganic peroxide compound comprises percarbonates.

* * * * *